(12) United States Patent
Schultz

(10) Patent No.: US 8,137,308 B2
(45) Date of Patent: Mar. 20, 2012

(54) CATHETER WITH ADJUSTABLE DEFLECTION SENSITIVITY

(75) Inventor: Jeffrey William Schultz, Chino, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 243 days.

(21) Appl. No.: 12/211,728

(22) Filed: Sep. 16, 2008

(65) Prior Publication Data

US 2010/0069834 A1    Mar. 18, 2010

(51) Int. Cl.
*A61M 25/092* (2006.01)

(52) U.S. Cl. .............. 604/95.04; 604/528; 600/585; 600/434

(58) Field of Classification Search .............. 604/95.04, 604/159, 280, 282, 170, 95.01, 500–533; 600/585, 433–434, 149
See application file for complete search history.

(56) References Cited

U.S. PATENT DOCUMENTS

| | | |
|---|---|---|
| 4,930,521 A | 6/1990 | Metzger et al. |
| 4,941,455 A | 7/1990 | Watanabe et al. |
| 4,942,866 A | 7/1990 | Usami |
| 4,947,827 A | 8/1990 | Opie et al. |
| 4,996,974 A | 3/1991 | Ciarlei |
| 5,195,968 A | 3/1993 | Lundquist et al. |
| 5,199,950 A | 4/1993 | Schmitt et al. |
| 5,273,535 A | 12/1993 | Edwards et al. |
| 5,325,845 A | 7/1994 | Adair |
| 5,328,467 A | 7/1994 | Edwards et al. |
| 5,358,478 A | 10/1994 | Thompson et al. |
| 5,363,861 A | 11/1994 | Edwards et al. |
| 5,626,553 A | 5/1997 | Frassica et al. |
| 5,676,653 A | 10/1997 | Taylor et al. |
| 5,891,088 A * | 4/1999 | Thompson et al. ........ 604/95.04 |
| 5,904,667 A | 5/1999 | Falwell |
| 6,030,360 A | 2/2000 | Biggs |

(Continued)

FOREIGN PATENT DOCUMENTS

DE    27 52 325 A1    11/1997

(Continued)

OTHER PUBLICATIONS

European Search Report for European Patent Application No. EP 09 17 0033 dated Nov. 26, 2009, 7 pages.

(Continued)

*Primary Examiner* — Quynh-Nhu H Vu
(74) *Attorney, Agent, or Firm* — Christie, Parker & Hale, LLP

(57) ABSTRACT

A catheter that provides bi-directional steering and allows for deflection sensitivity adjustment includes a catheter body, a deflectable tip section and a control handle, wherein the control handle has a deflection member adapted for user manipulation, a deflection assembly responsive to the deflection member to draw on a tensile puller member for deflecting the tip section, and an adjustment mechanism adapted to adjust sensitivity of the deflection member. The adjustment mechanism also correspondingly adjusts a maximum degree of deflection of the tip section. The deflection assembly includes a rotatable pulley arm and two pulleys, and a deflection sensitivity adjustment mechanism with a cam device that varies a separation distance between the pulleys. The cam device is internally located in the pulley arm and is rotatable via deflection sensitivity knob by the user to increase the separation distance for greater deflection sensitivity in a deflection member user interface, or to decrease the separation distance for greater maximum degree of tip deflection.

18 Claims, 12 Drawing Sheets

U.S. PATENT DOCUMENTS

| | | | |
|---|---|---|---|
| 6,033,378 | A | 3/2000 | Lundquist et al. |
| 6,171,277 | B1 * | 1/2001 | Ponzi .................. 604/95.04 |
| 6,198,974 | B1 | 3/2001 | Webster, Jr. |
| 6,210,407 | B1 | 4/2001 | Webster |
| 6,213,974 | B1 | 4/2001 | Smith et al. |
| 6,224,609 | B1 | 5/2001 | Ressemann et al. |
| 6,440,062 | B1 | 8/2002 | Ouchi |
| 6,485,455 | B1 | 11/2002 | Thompson et al. |
| 6,530,897 | B2 | 3/2003 | Nardeo |
| 6,579,278 | B1 | 6/2003 | Bencini |
| 6,648,875 | B2 * | 11/2003 | Simpson et al. ............. 604/528 |
| 6,652,506 | B2 | 11/2003 | Bowe et al. |
| 7,008,401 | B2 * | 3/2006 | Thompson et al. ........ 604/95.04 |
| 7,025,759 | B2 | 4/2006 | Muller |
| 7,269,453 | B2 | 9/2007 | Mogul |
| 7,377,906 | B2 * | 5/2008 | Selkee .................. 604/95.04 |
| 7,591,799 | B2 * | 9/2009 | Selkee .................. 604/95.04 |
| 2003/0135199 | A1 | 7/2003 | Rosenman et al. |
| 2005/0021003 | A1 | 1/2005 | Caso et al. |
| 2005/0277874 | A1 * | 12/2005 | Selkee .................. 604/95.04 |
| 2005/0277875 | A1 * | 12/2005 | Selkee .................. 604/95.04 |
| 2006/0184107 | A1 * | 8/2006 | Bencini et al. ............. 604/95.04 |
| 2007/0232858 | A1 | 10/2007 | Macnamara et al. |
| 2008/0009791 | A1 | 1/2008 | Cohen et al. |
| 2008/0065011 | A1 | 3/2008 | Marchand et al. |
| 2008/0103520 | A1 * | 5/2008 | Selkee .................. 606/195 |
| 2008/0319420 | A1 * | 12/2008 | Rosenman et al. ........... 604/528 |
| 2009/0234280 | A1 * | 9/2009 | Tah et al. .................... 604/95.04 |
| 2010/0168827 | A1 * | 7/2010 | Schultz .................. 607/116 |

FOREIGN PATENT DOCUMENTS

| | | |
|---|---|---|
| EP | 1 607 118 A1 | 12/2005 |
| EP | 1 607 119 A1 | 12/2005 |
| WO | WO 94/26347 | 11/1994 |

OTHER PUBLICATIONS

European Patent Office Search Report and Annex to European Search Report for EP 09 25 2919.7 completed Jun. 30, 2010, mailed Jul. 15, 2010, 10 pages.

* cited by examiner

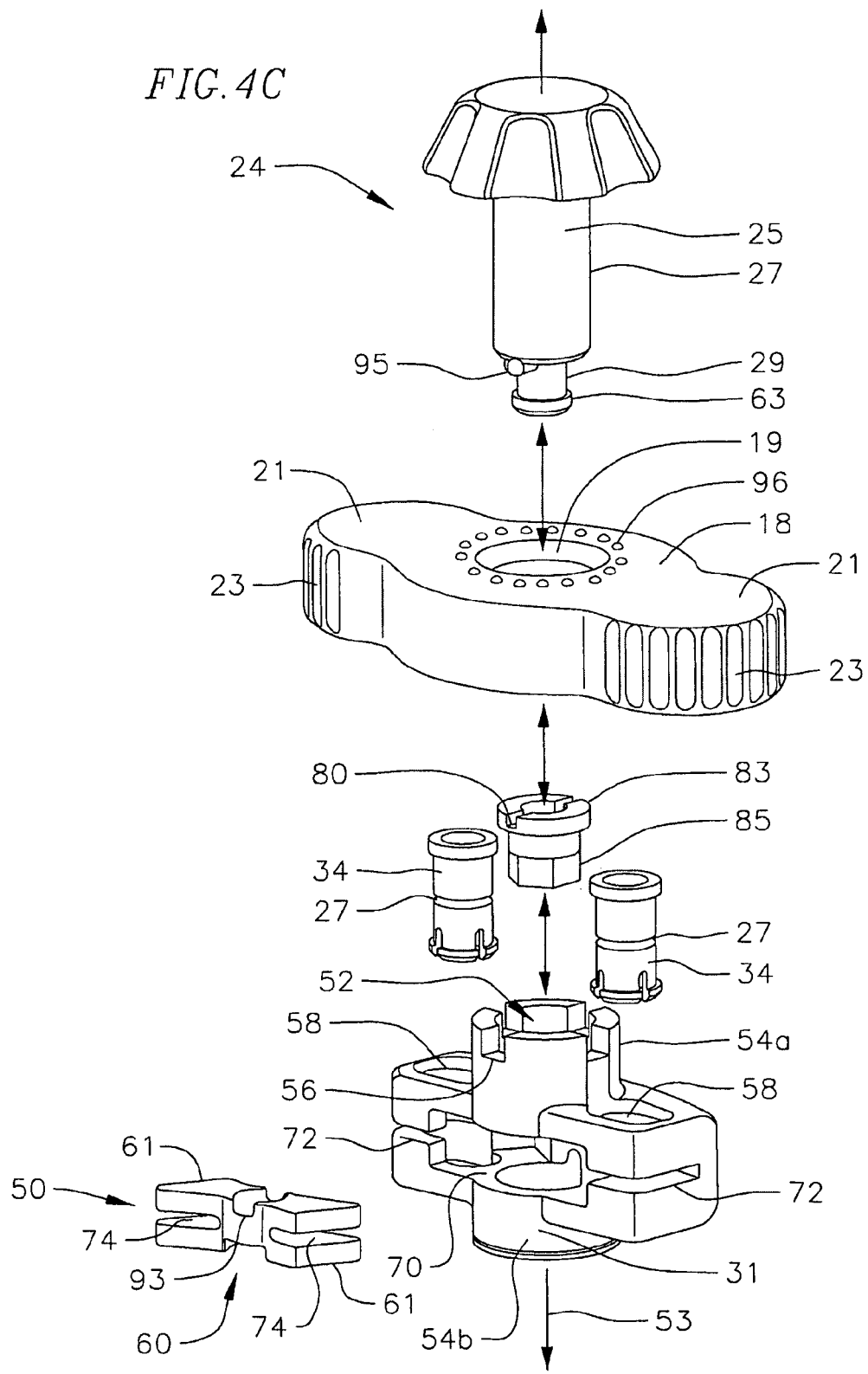

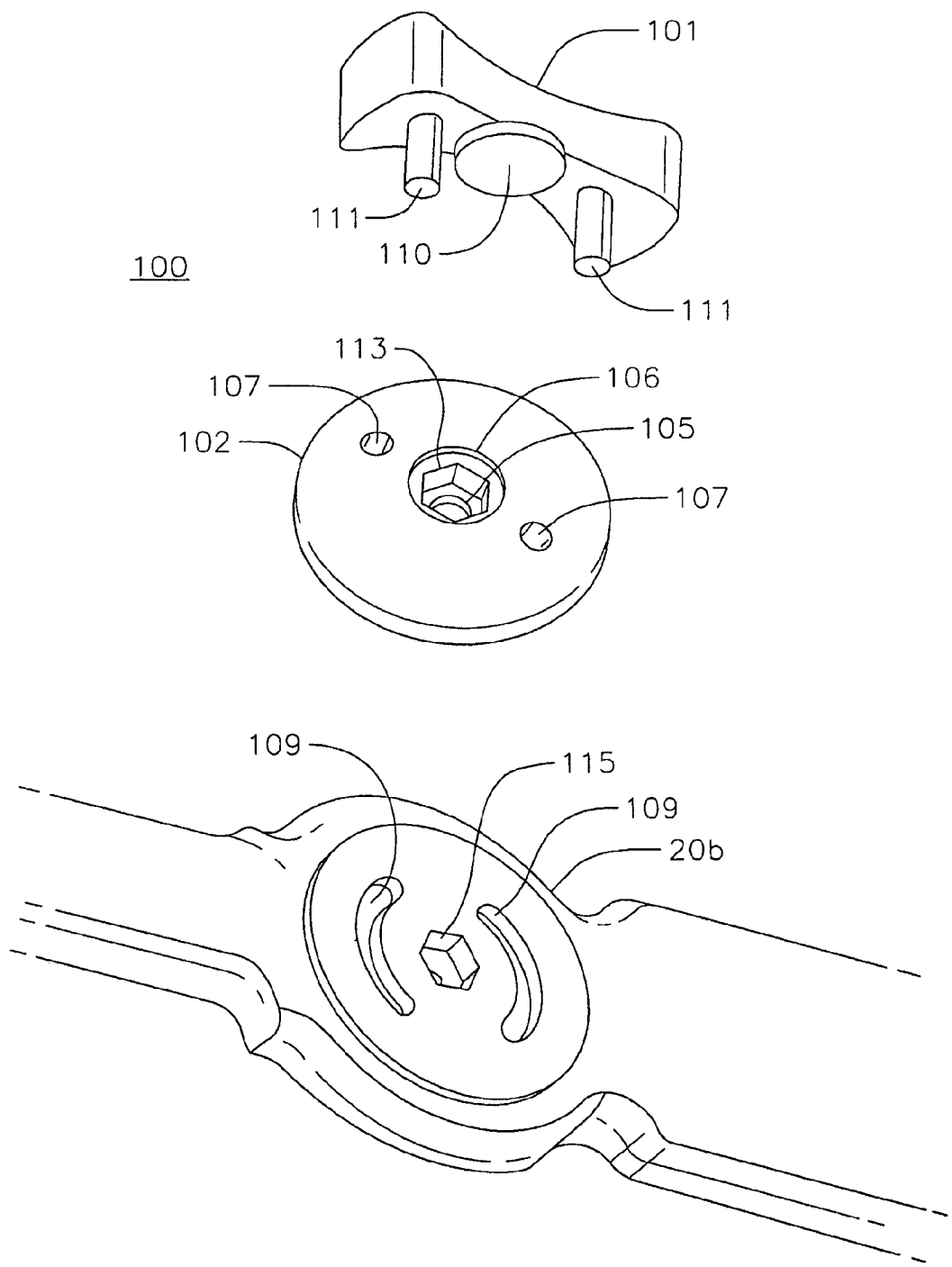

CATHETER WITH ADJUSTABLE DEFLECTION SENSITIVITY

FIELD OF INVENTION

The present invention relates to catheters and in particular deflectable catheters with control handles.

BACKGROUND OF INVENTION

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Bidirectional catheters have been designed to be deflectable in one direction by one puller wire and in the opposite direction within the same plane by a second puller wire. In such a construction, the puller wires extend into opposing off-axis lumens within the tip section of the catheter. So that the tip section can bend in both directions in the same plane, the puller wires and their associated lumens are located along a diameter of the tip section. For ablation catheters, electrode lead wires are also provided within the distal end and typically, an additional lumen is used to contain the electrode lead wires. For example, U.S. Pat. No. 6,210,407, is directed to a bi-directional catheter comprising two puller wires and a control handle having at least two movable members longitudinally movable between first and second positions. As another example, U.S. Pat. No. 6,171,277 is directed to a bidirectional steerable catheter having a control handle that houses a generally-circular spur gear and a pair of spaced apart rack gears. Each rack gear is longitudinally movable between first and second positions, whereby proximal movement of one rack gear results in rotational movement of the spur gear, and correspondingly distal movement of the other rack gear. Also known is U.S. Pat. No. 6,198,974 which is directed to a bi-directional electrode catheter comprising a control handle. At their proximal ends, two pairs of puller wires are attached to movable pistons in the control handle. Each piston is controlled by an operator using a slidable button fixedly attached to each piston. Movement of selected buttons results in deflection of the tip section into a generally planar "U"- or "S"-shaped curve. Further known is U.S. Pat. No. 5,891,088 directed to a steering assembly with asymmetric left and right curve configurations. Proximal ends of left and right steering wires are adjustably attached to a rotatable cam housed in a control handle. The rotatable cam has first and second cam surfaces which may be configured differently from each other to accomplish asymmetric steering.

Also known are control handles that provide a greater degree of deflection in the catheter tip. For example, U.S. Pat. No. 7,377,906, the entire disclosure of which is hereby incorporated by reference, has increased throw capacity through the use of pulleys around which puller wire travel for minimized offset angle between the puller wire and the longitudinal axis of the control handle while maximizing the travel distance of that puller wire for any given distance traveled by the pulley drawing the puller wire. Suitable tensile puller members are described in U.S. Patent Publication No. 2008/0103520, the entire disclosure of which is also hereby incorporated by reference.

However, it is desirable to provide a control handle that allows user adjustability of the maximum degree of deflection as well as deflection sensitivity of the control handle to user manipulations, as needed for different uses and applications.

SUMMARY OF THE INVENTION

A catheter that provides bi-directional steering and allows for deflection sensitivity adjustment includes a catheter body, a deflectable tip section and a control handle, wherein the control handle has a deflection member adapted for user manipulation, a deflection assembly responsive to the deflection member to draw on a tensile puller member for deflecting the tip section, and an adjustment mechanism adapted to adjust sensitivity of the deflection member. The adjustment mechanism also correspondingly adjusts a maximum degree of deflection of the tip section.

In a more detailed embodiment, the catheter includes a deflection assembly having a rotatable pulley arm and two pulleys, and a deflection sensitivity adjustment mechanism having a cam device that varies a separation distance between the pulleys. The cam device is internally located in the pulley arm and is rotatable via deflection sensitivity knob by the user to increase the separation distance for greater deflection sensitivity in a deflection member user interface, or to decrease the separation distance for greater maximum degree of tip deflection. The cam device shares a common axis of rotation with the pulley arm of the deflection assembly and can be manipulated by a deflection knob rotatable by a user.

The tensile puller members by which deflection is accomplished may include a fiber portion that engages the pulleys of the deflection assembly for improved durability against bending stresses from repeated deflections of the tip section.

The catheter may also include a deflection tension adjustment mechanism to allow user adjustment of the tension of the deflection member by increasing or decreasing a resistance to rotation of the deflection member.

The present invention may be used for both uni- and bi-directional catheters and the cam device is adaptable to provide different ranges in deflection sensitivity and maximum deflection.

BRIEF DESCRIPTION OF THE DRAWINGS

These and other features and advantages of the present invention will be better understood by reference to the following detailed description when considered in conjunction with the accompanying drawings wherein:

FIG. 4C is an exploded view of the assembly of FIG. 4.

FIG. 6 is an exploded view of an embodiment of a deflection arm tension mechanism.

DETAILED DESCRIPTION OF THE INVENTION

Figure 1:
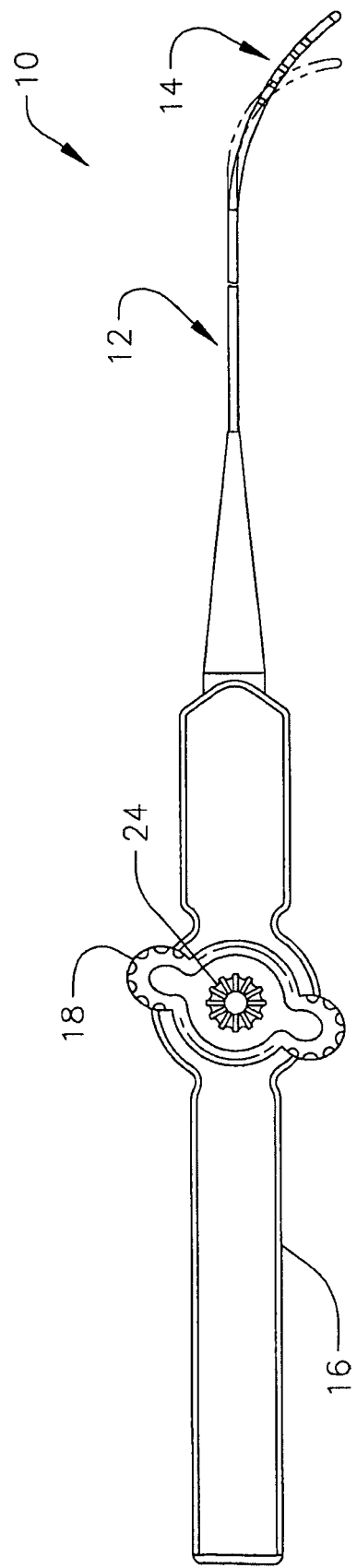
FIG. 1 is a top view of an embodiment of the catheter of the present invention.

An embodiment of a steerable bidirectional catheter 10 with adjustable deflection sensitivity is illustrated in FIG. 1 The catheter 10 comprises an elongated catheter body 12 having proximal and distal ends, a tip section 14 at the distal end of the catheter body 12, and a control handle 16 at the proximal end of the catheter body 12. For deflecting the deflectable section 14, the catheter 10 has puller members that extend from the control handle, through the catheter body 12 and into the deflectable section 14. Distal ends of the puller members are anchored in the deflectable section 14 and their proximal ends are anchored in the control handle. Longitudinal movement of the puller members relative to the catheter body 12, which results in deflection of the tip section 14, is accomplished by manipulation of a deflection arm 18 on the control handle 16. Moreover, a deflection sensitivity knob 24 is included on the control handle to allow user adjustment of the amount of maximum deflection, as well as the sensitivity of deflection adjustment.

Figure 2A:
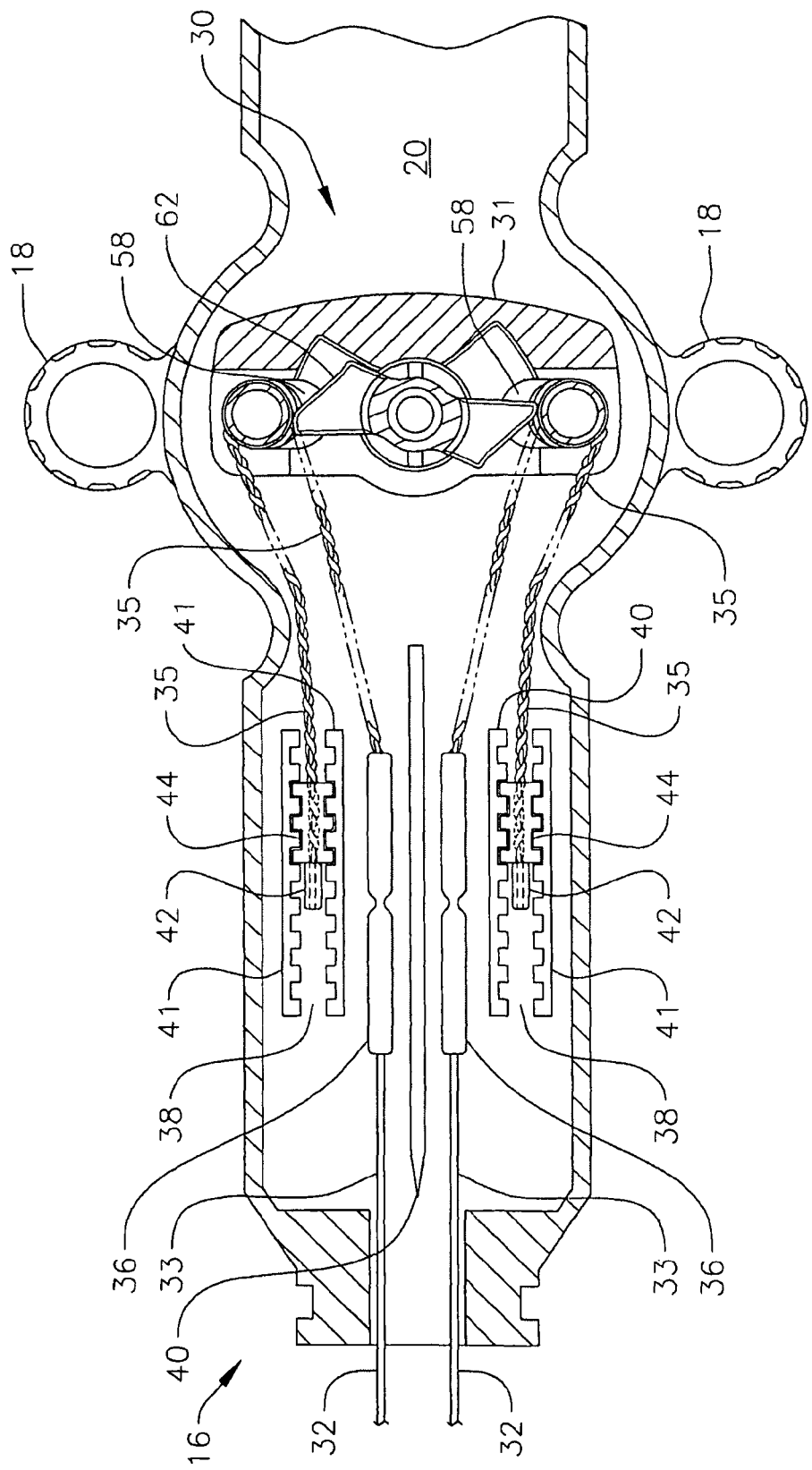
FIG. 2a is top view of an embodiment of a housing half of the control handle with a deflection assembly in one position where a separation distance between a pair of pulleys is at a maximum FIG. 2b. is top view of the housing half of FIG. 2, where the separation distance is at a minimum.
Figure 2B:
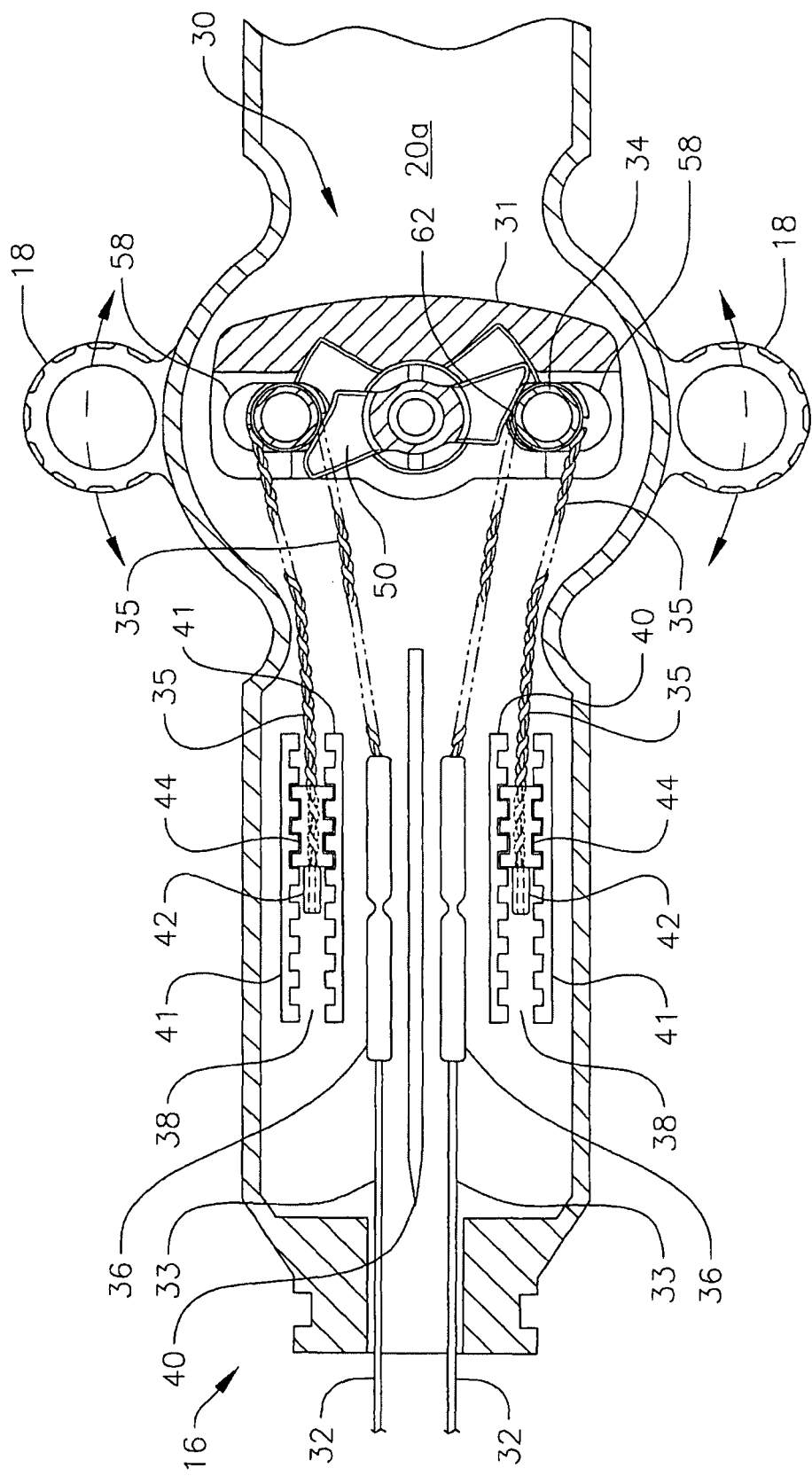

With reference to FIGS. 1, 2a and 2b, the control handle 16 comprises a generally elongated handle housing 20, which can be made of any suitable rigid material. In the illustrated embodiment, the housing includes two opposing halves 20a and 20b that are joined by glue, sonic welding or other suitable means along a longitudinal peripheral seam around the housing. The control handle 16 comprises a deflection assembly 30 that is responsive to the deflection arm 18 and the deflection sensitivity knob 24 to control deflection of the tip section 14.

Figure 3A:
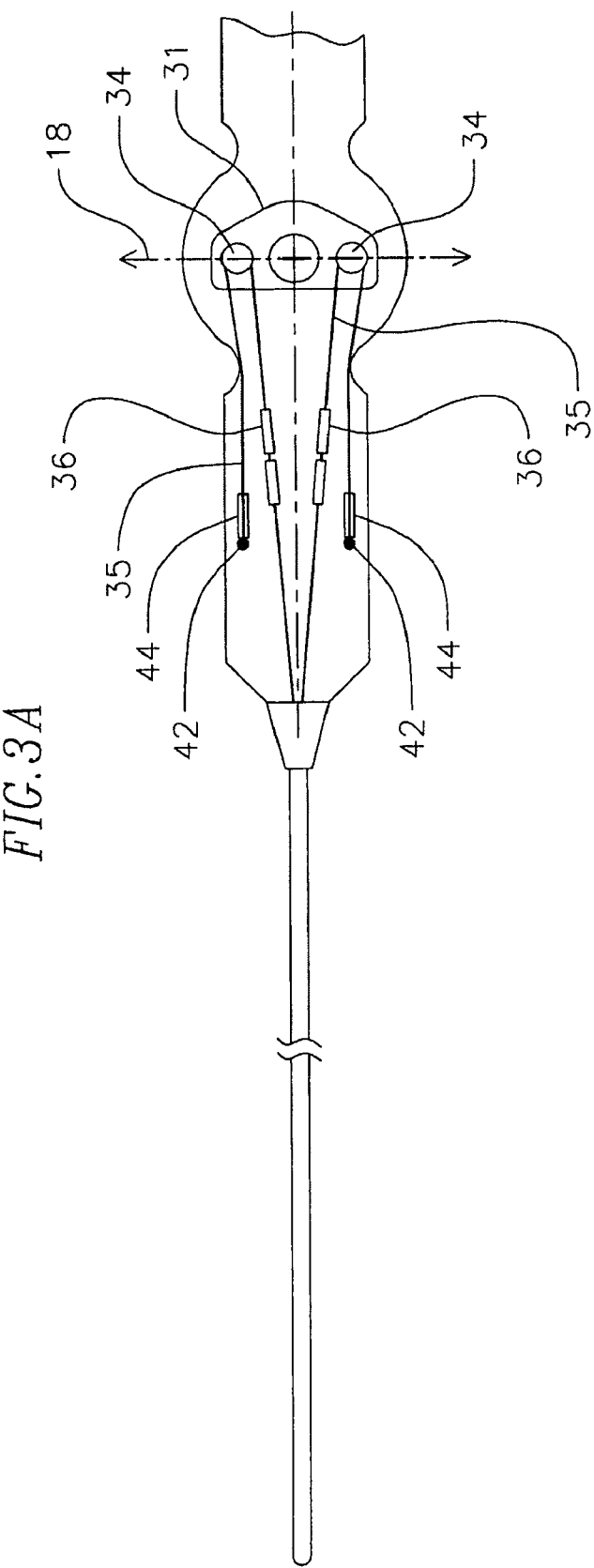
FIGS. 3a-3c show positions of an embodiment of the deflection assembly and puller wires in a neutral position, deflection to the right and deflection to the left.
Figures 3B, 3C:
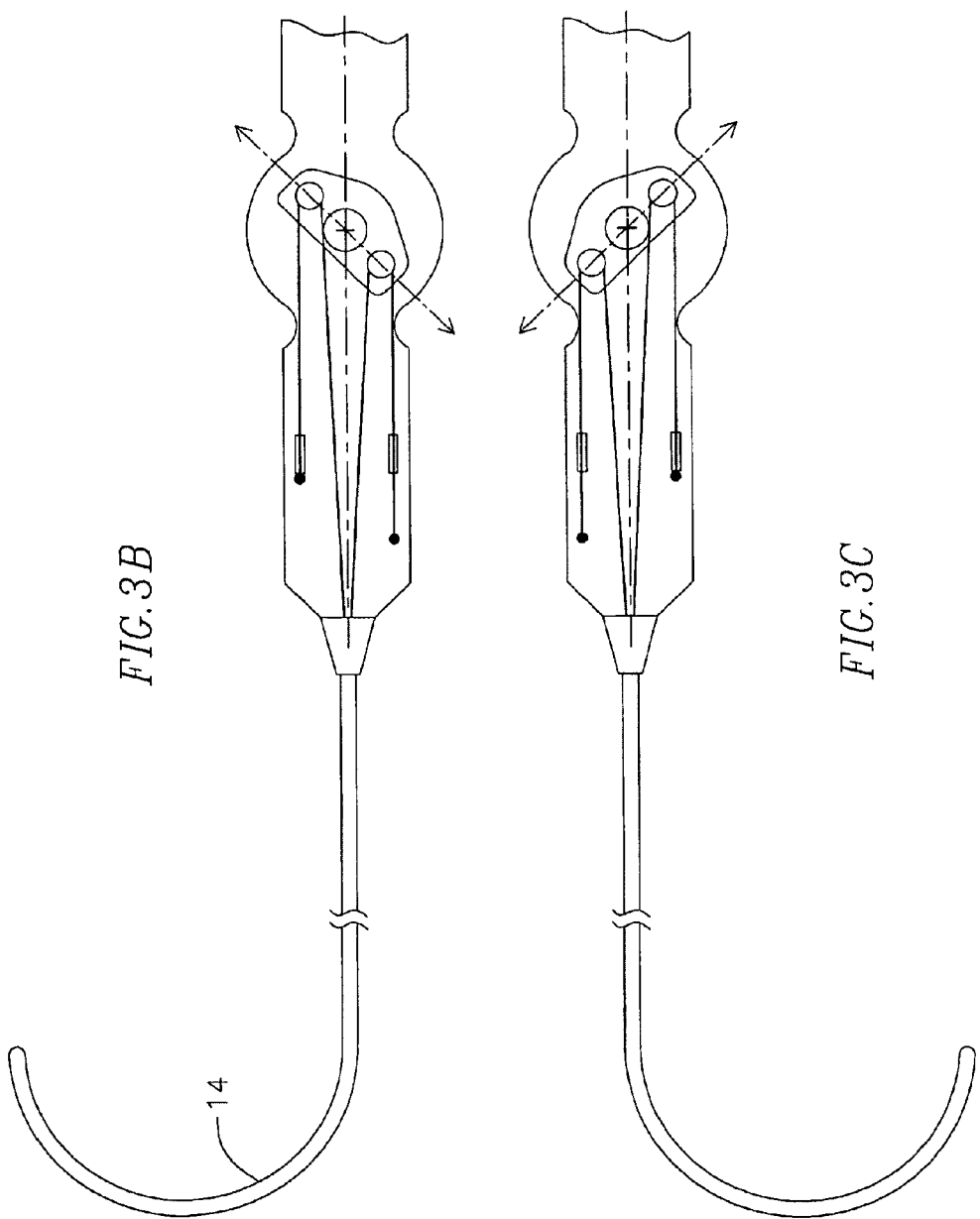
Figure 4:
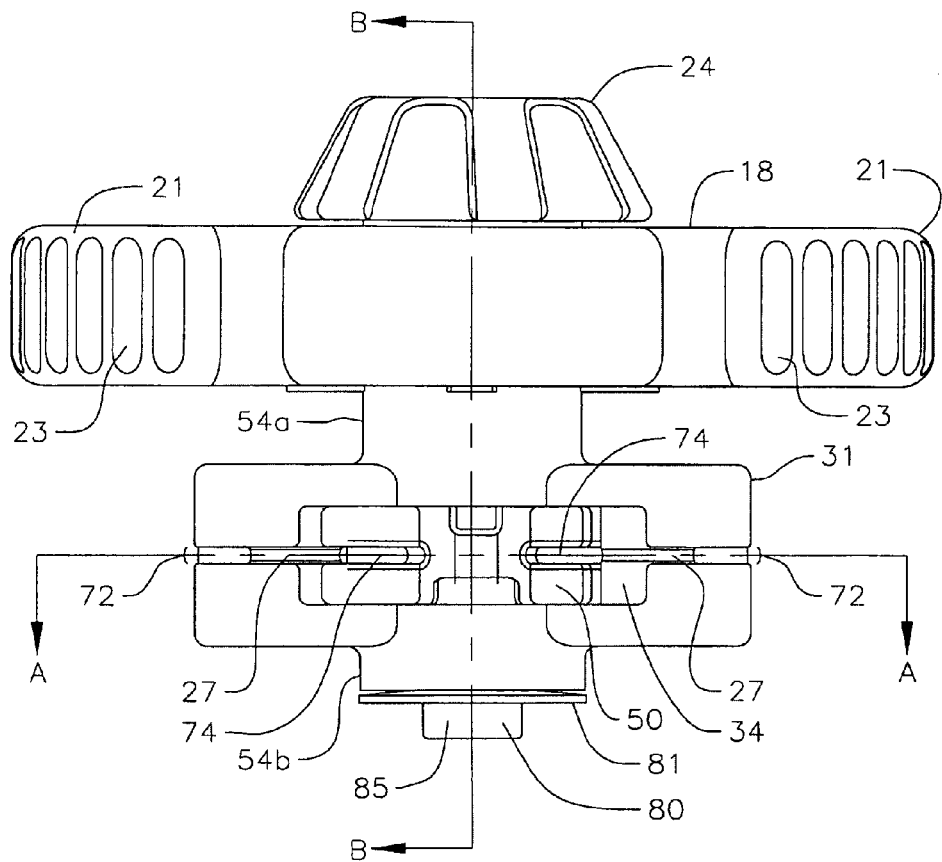
FIG. 4 is a side elevational view of an embodiment of an assembly of the deflection assembly, the deflection arm and a deflection sensitivity knob (with control handle housing not shown).
Figure 4A:
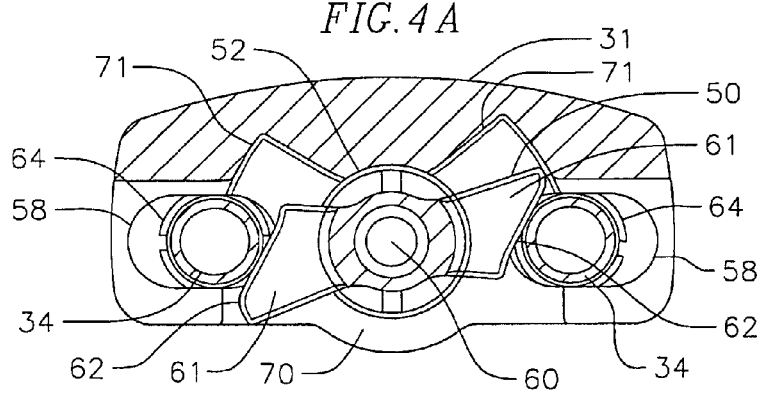
FIG. 4A is a cross-sectional view of the assembly of FIG. 4, taken along line A-A.
Figure 4B:
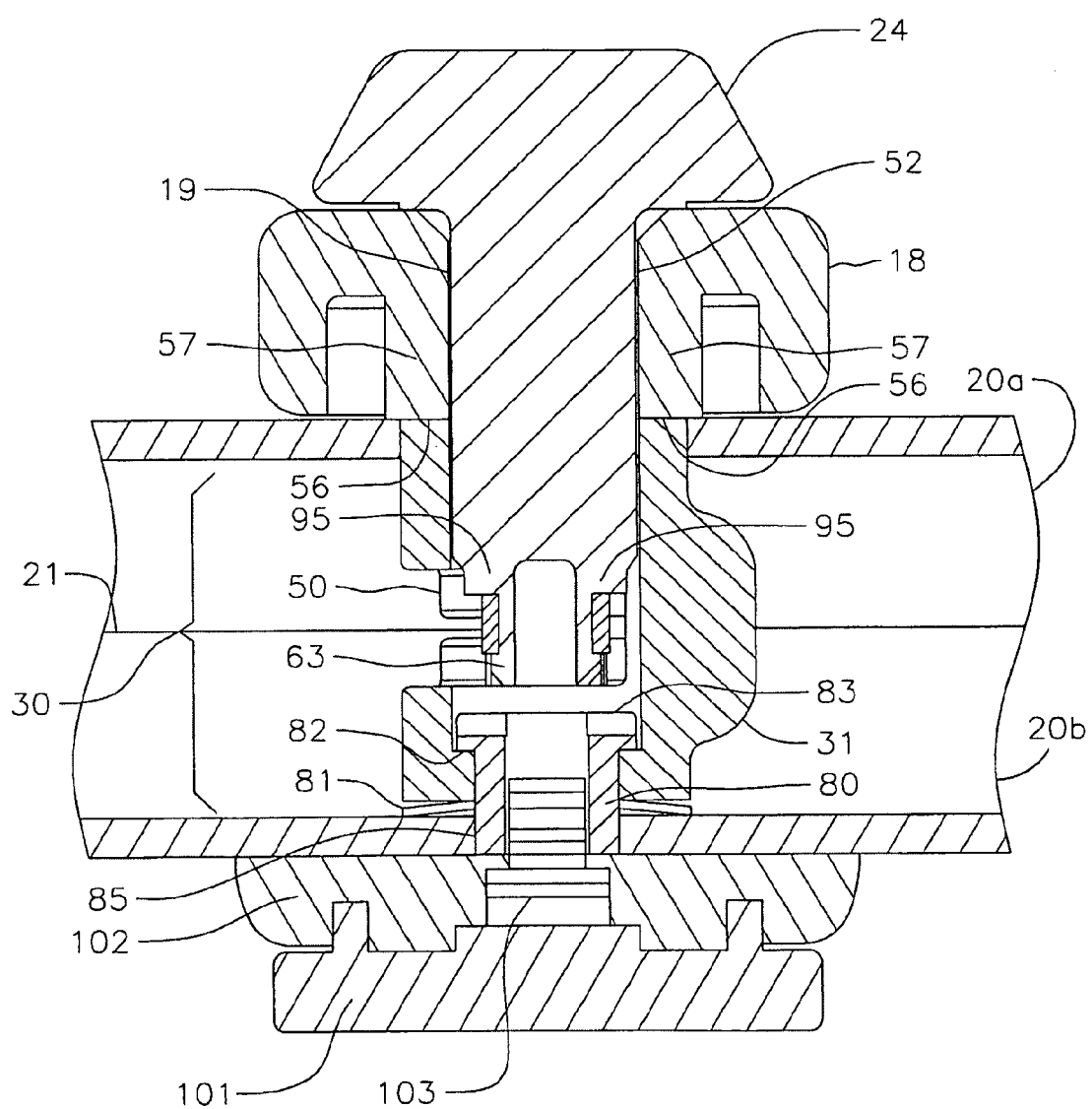
FIG. 4B is a cross-sectional view of the assembly of FIG. 4, taken long line B-B, shown with control handle housing.
Figure 5:
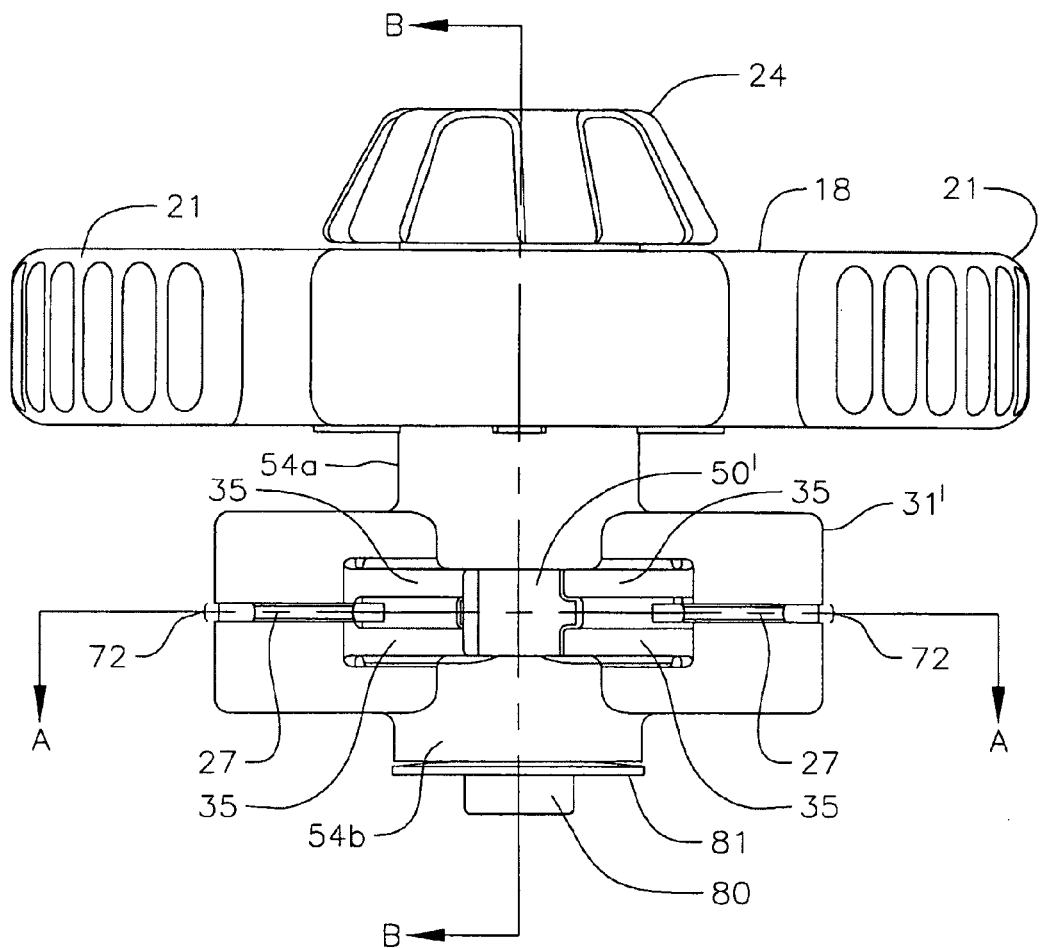
FIG. 5 is a side elevational view of an alternate embodiment of an assembly of the deflection assembly, the deflection arm and a deflection sensitivity knob (with control handle housing not shown).
Figure 5A:
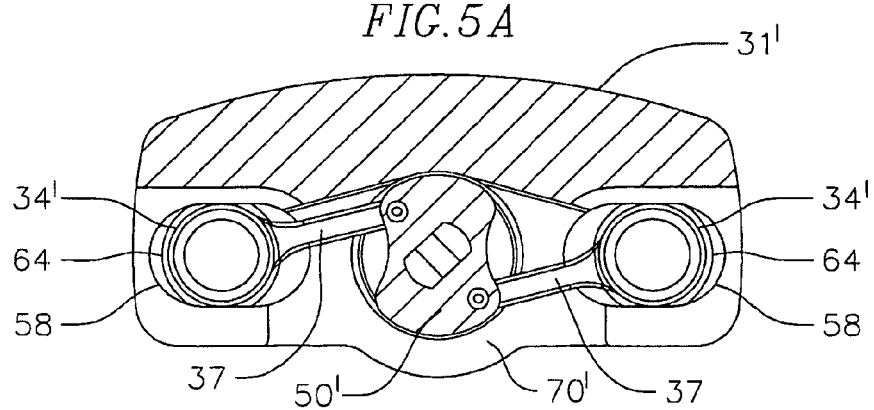
FIG. 5A is a cross-sectional view of the assembly of FIG. 5, taken along line A-A.
Figure 5B:
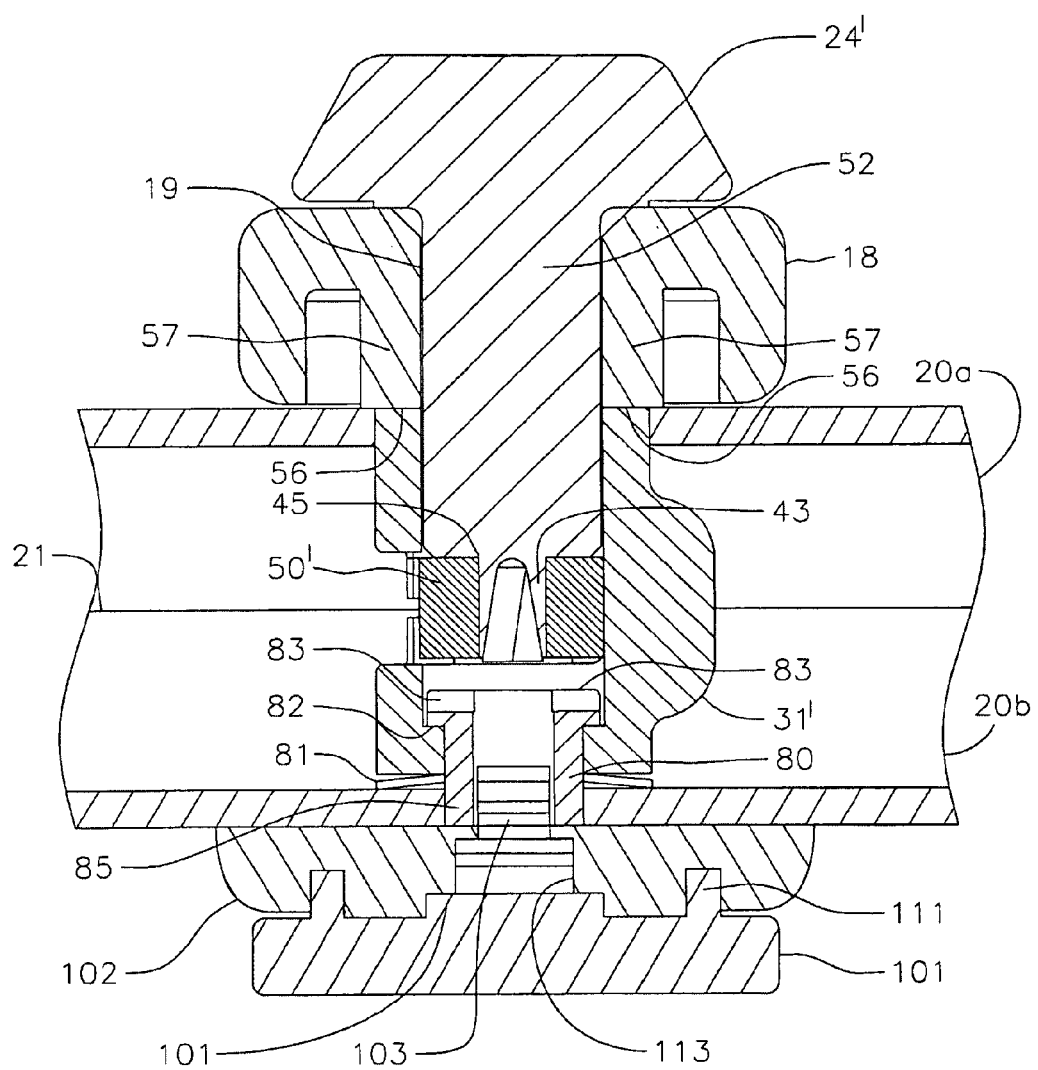
FIG. 5B is a cross-sectional view of the assembly of FIG. 5, taken long line B-B, shown with control handle housing.
Figure 5C:
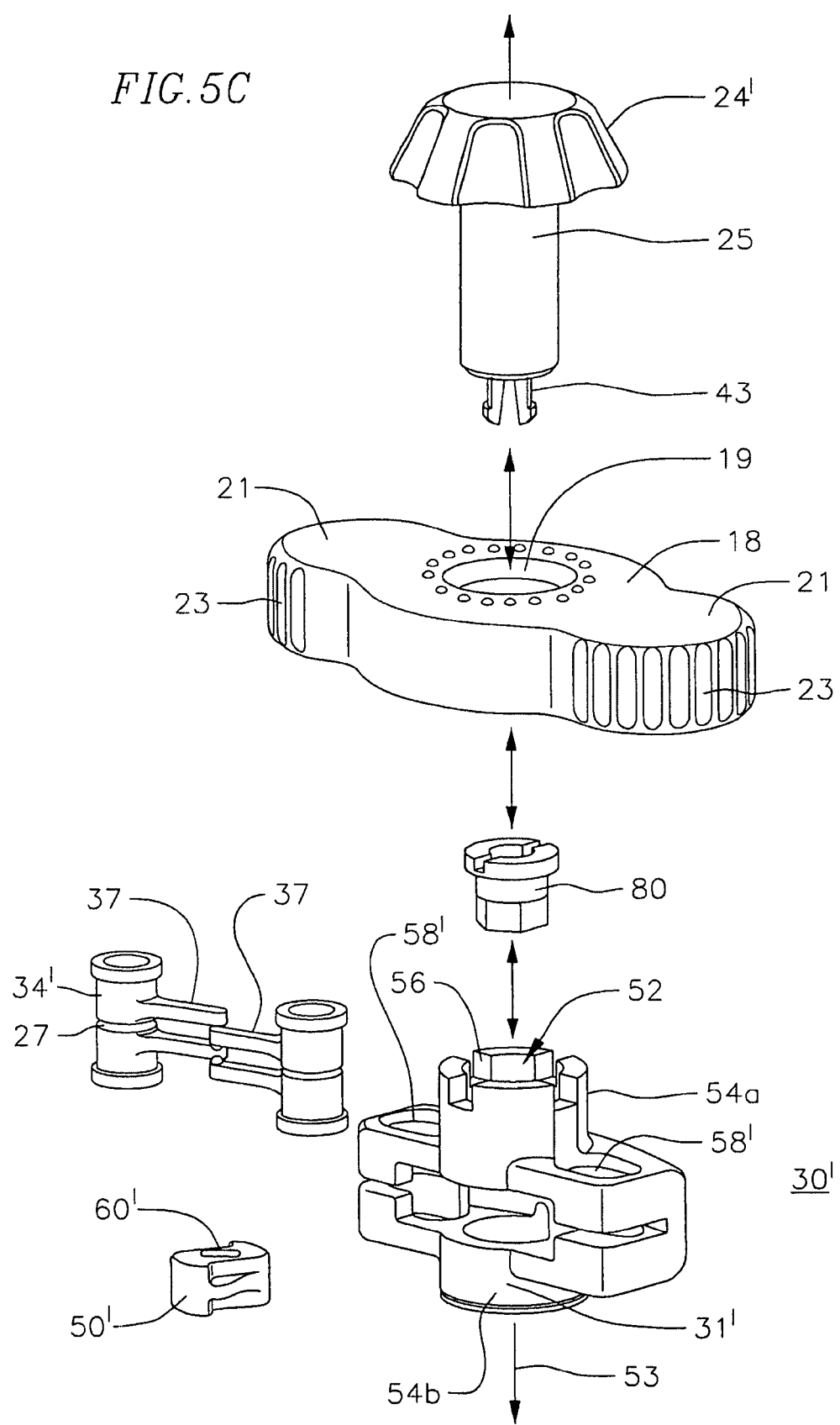
FIG. 5C is an exploded out peripheral view of the assembly of FIG. 5.

In the illustrated embodiment of FIGs. of 2a and 2b, the deflection assembly 30 has a pulley arm 31 with a pair of pulleys 34 (for example, snap bearings) that act on tensile puller members 32 to deflect the tip section 14. The deflection arm 18 and the pulley arm 31 are rotationally coupled such that rotation of the deflection arm by a user rotates the pulley arm. As the pulley arm 31 is rotated by means of the deflection arm 18, the pulleys 34 are displaced from a neutral position (FIG. 3a) with one pulley drawing a puller member 32 on one side of the catheter against its anchored proximal end for deflecting the distal section 14 toward that side (FIGS. 3b and 3c).

Each tensile puller member 32 may be a connected or segmented puller member having multiple tensile puller members that are joined in series. In the illustrated embodiment of FIGS. 2a and 2b, each puller member 32 has a distal puller wire portion 33 and a proximal tensile fiber portion 35 such that the puller wire portion 33 extends from the control handle 16 to the deflectable section 14 and the proximal tensile fiber 35 engages the respective pulley 34 in the control handle 16. In this manner, it is the more flexible tensile fiber portion 35 that interacts with the pulley and undergoes repeated bending and straightening during deflection operations. The tensile fibers 35 thus save the puller wires 33 from bending stress imposed fatigue failure caused by the pulleys 34.

Each puller wire portion or puller wire 33 is made of any suitable metal, such as stainless steel or Nitinol. Preferably each puller wire 33 has a low friction coating, such as a coating of Teflon® or the like. Each puller wire 33 has a diameter preferably ranging from about 0.006 inch to about 0.012 inch. Preferably both of the puller wires 33 have the same diameter. Each tensile fiber portion or tensile fiber 35 may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys 34 and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions. The puller wire 33 and the tensile fiber 35 are connected or secured to each other by a connector 36, e.g., a crimped brass ferrule covered by shrink tubing.

The puller members 32 enter the control handle 16 at its distal end. An elongated divider 40 is situated between the two puller members 32 to define separate paths toward the pulley arm 31. The connectors 36 between the puller wire 33 and tensile fiber 35 of the puller members are situated distal of the pulleys 34 so they do not interfere with the deflection assembly 30. Proximal of the connectors 36, each tensile fiber 35 is trained around a respective pulley 34 and extends between a respective channel 38 defined by a respective pair of racks 41. A proximal end of each tensile fiber is encased within a molded member or slug 42 sized to fit in and to translate in the channel 38. Proximal the slug 42s are stops or clips 44 that are adjustably positioned in a selected location along the racks 41, for example, by means of interlocking teeth formed in the racks 41 and the clips 44 to releasably lock in the selected position against movement. The clips 44 are formed so that each respective tensile fiber 35 can slide through them, below or around them but the clips block the slugs 42 from moving proximally past them. Accordingly, the clips 44 limit the proximal movement of the slugs 42 and serve as anchors for the proximal ends of the tensile fibers 35 to effectuate deflection when each is drawn proximally by the deflection assembly 30.

During assembly of the control handle 16 before the two housing halves 20a and 20b are joined, the clip stops 44 are selectively positioned between the racks 41 to achieve a desirable tension in each puller member 32. The interlocking teeth of the racks 41 and clip stops 44 allow for fine adjustments in setting the tension.

As described, each puller member 32 is trained around a respective pulley 34 of the pulley arm 31 of the deflection assembly 30 so that rotation of the deflection arm 18 causes a pulley 34 on one side to draw on its puller member for deflecting the catheter tip 14 toward that side (FIGS. 3*b* and 3*c*). Moreover, the deflection assembly 30 advantageously allows a user to set a deflection sensitivity and adjust the maximum degree of deflection via the deflection sensitivity knob 24. In particular, the deflection sensitivity knob 24 controls a cam device 50 that allows the deflection sensitivity to decrease with corresponding increase in the maximum degree of deflection (FIG. 2*a*) or the deflection sensitivity to increase with corresponding decrease in the maximum degree of deflection (FIG. 2*b*). As described further below, the cam device 50 sits within the pulley arm 31 so as to set the pulleys with a selected separation distance.

As better shown in the illustrated embodiment of FIGS. 4, 4*a*-4*c*, the pulley arm 31 of the deflection assembly 30 has a central core opening 52 defined by annular ends 54*a* and 54*b*. A center of the opening 52 defines a rotation axis 53 of the deflection assembly 30 (also referred to as the throw axis of the control handle). Annular end 54*a* has recesses 56 that interlock with protrusions 57 (FIG. 4*b*) formed on an underside of the deflection arm 18 so that the pulley arm 31 is rotationally coupled to the deflection arm 18 for deflecting the catheter tip section 14.

On opposite ends of the pulley arm 31 and generally equidistant from the core opening 52 are two holes 58, in each of which sits a pulley 34. The holes have an elongated cross-section so that the pulleys 34 can be moved about within the holes by the cam device 50 in response to the deflection sensitivity knob 24. The user thus uses the deflection knob 24 to set the separation distance of the pulleys 34 between a maximum and a minimum. The maximum separation distance (FIG. 2*a*) provides decreased deflection sensitivity in the deflection arm 18 but an increased maximum degree of deflection in the tip section 14. The minimum separation distance (FIG. 2*b*) provides increased deflection sensitivity in the deflection arm 18 but a decreased maximum degree of deflection in the tip section 14 (FIG. 2*b*).

The cam device 50 is situated within a cavity 70 of the pulley arm 31 that is formed with cutouts 71 to accommodate rotation of the cam device. The cam device 50 has a centered opening 60 that is aligned with the opening 52 of the pulley arm 31 so that the cam device 50 and the pulley arm 31 have share the rotation axis 53. The pulleys 34 are snap-fitted into the holes 58 of the pulley arm 31. The tensile puller members 32 enter the pulley arm 31 through slots 72 in the pulley arm 31 and slots 74 of the cam device 50 and are wrapped around a groove 27 formed in a respective pulley 34.

In the illustrated embodiment of FIGS. 4, 4*a*-4*c*, the cam device 50 has two opposing, generally triangular portions or wings 61 having an outer edge 62 that is in contact with an adjacent pulley 34. The edge 62 is angled with a predetermined curvature so that the cam device 50 when rotated pushes the pulleys 34 in a predetermined manner (to provide a predetermined "feel" in the knob 24) to an outermost position (Position A) (FIG. 2*a*) or allow the pulleys to be moved to an innermost position (Position B) (FIG. 2*b*) under a force of a biasing member 64, such as a spring or an elastic band. In accordance with the present invention, a user adjusts the separation distance of the pulleys 34 by rotating the cam device 50 via the deflection sensitivity knob 24. In the illustrated embodiment of FIGS. 2*a* and 2*b*, rotating the cam device 50 in the clockwise direction increases the distance between the pulleys 34, and rotating the cam device 50 in the counterclockwise direction decreases the distance. Where the pulleys 34 are set in Position A (FIG. 2*a*), the pulleys experience a larger radius of action with rotation of the pulley arm 31 which results in a maximum degree of catheter deflection in the tip section 14 but minimum deflection sensitivity in the deflection arm 18. Where the pulleys 34 are set in Position B (FIG. 2*b*), the pulleys experience a smaller radius of action with rotation of the pulley arm 34 which results in a minimum degree of catheter deflection in the tip section 14 but maximum deflection sensitivity in the deflection arm 18. Where the pulleys 34 are set somewhere in between Positions A and B, the pulleys experience a radius of action providing a lesser degree of deflection in the tip section 14 but greater deflection sensitivity in the deflection arm 18, or vice versa.

The deflection arm 18 which is rotationally coupled to the pulley arm 31 by means of interlocking formations 56 and 57 has a central opening 19 which is also aligned with the openings 52 and 60 of the pulley arm 31 and the cam device 50 in sharing the common rotation axis 53. The deflection arm has two rounded ends 21, each having with a friction-inducing surface 23 for an operator use to in rotating deflection arm to deflect the catheter tip 24.

Extending into the openings 19, 52 and 60 is a stem 25 of the deflection sensitivity knob 24. The stem has a longer, thicker proximal portion 27 and a shorter, thinner distal portion 29. The proximal stem portion 27 reaches into the opening 60 of the cam device 50, where a nub 63 on a distal tip of the stem snap-fits or otherwise engages a neck 91 in the opening 60 of the cam device so as to lock the deflection sensitivity knob 24 to the cam device 50 and hence to the deflection assembly 30. Two diametrically opposed protrusions or keys 95 formed on the distal stem portion 29 are received in notches 93 formed in the cam device 50 to align and rotationally couple the knob 24 with the cam device 50. Accordingly, rotation of the deflection sensitivity knob 24 rotates the cam device 50 for setting the separation distance between the pulleys 34 and their radius of action about the throw axis 53.

To maintain the position or setting of the knob 24 relative to the deflection arm 18, a friction-inducing surface 96 (e.g., with detents) is formed on a contact surface between the knob and the deflection arm, such as an interfacing surface of the knob and the deflection arm. Alternatively, the friction-inducing surface can be formed on the stem 25 and/or an inner surface of the opening 52 of the pulley arm 31. In any case, the friction-inducing surface enables the deflection sensitivity knob 25 to remain in a position selected by the user and to remain in that position while the user rotates the deflection arm 18 to deflect the catheter tip 14.

In the alternative embodiment of FIGS. 5, 5*a*-5*c*, a deflection assembly 30' has a cam device 50' that has a generally rectangular form with spiraling corners, and pulleys 34' have linkages 37 whose ends are pivotally attached to opposing corners of the cam device 50'. With rotation of the cam device, the corners move to pull or push the linkages 37 which position the pulleys 34' between the outermost position and the innermost position in holes 58'. Thus, in a similar manner, the pulleys 34' experience different radii of action with rotation of pulley arm 31' in response to the setting of deflection sensitivity knob 24'.

The cam device 50' is received within a cavity 70' of the pulley arm 31' that is formed to accommodate rotation of the cam device within the pulley arm. The pulleys 34' are inserted into the holes 58' of the pulley arm, which are sized to fit the linkages 37. Like the other embodiment, the slots 72 are provided in the pulley arm 31' so that a tensile puller member 32 can be wrapped around the groove 27 each pulley 34'.

The deflection arm 18 and the pulley arm 31' are likewise rotationally coupled by means of the interlocking formations 57 and 56 in the deflection arm 18 and the pulley arm 31', respectively. And, extending into the openings 19 and 52 of the deflection arm 18 and pulley arm 31' is a stem 25' of the deflection sensitivity knob 24. The stem 24' has the proximal portion 27, but extending therefrom are alignment prongs 43 that extend through a slot opening 60' (FIG. 5c) of the cam device 50' where they fasten to an edge of the opening 60' to align and lock the knob 24' with the cam device 50' for rotational coupling. Accordingly, rotation of the deflection sensitivity knob 24' rotates the cam device 50' for setting the separation distance between the pulleys 34' and their radius of action about the throw axis 53. Likewise, a friction-inducing surface 69 (e.g., with detents) can be formed on a contact surface between the knob 24' and the deflection arm 18.

For either of the foregoing embodiments, the control handle 16 further includes a deflection arm tension adjustment mechanism 100 that is mounted on the housing half 20b to oppose the deflection arm 18 and the deflection sensitivity knob 28 mounted on the housing half 20a. The illustrated embodiment of the tension adjustment mechanism of FIG. 6 includes an adjustment dial 101, a cap 102, a tension screw 103, a friction nut 80 and a washer 81. A user rotates a dial 101 to adjust the tightness or tension of the rotational movement of deflection arm 18 by compressing or releasing pulley arm 31 against the washer 81. The friction nut 80 is situated at one end of the core opening 52 of the pulley arm 31. The nut 80 is placed in the opening 52 of the pulley arm before the cam device 50 and knob 24 are assembled with the pulley arm. There is a smaller inner circumference along the opening 52 to form a neck 82 against which a head 83 of the friction nut abuts so that an end 85 of the nut with a hexagonal cross-section extends out of the annular end 54. The housing half 20b provides a hole 115 with a matching hexagonal cross-section to receive the end 85.

The cap 102 is fastened to the housing half 20b and also the housing half 20b to the housing half 20a by the tension screw 103 whose end is inserted through an opening 105 in the cap and screwed into the exposed end 95 of the friction nut 80. The dial 101 is fastened to the cap 102 by two prongs 111 that extend through holes 106 and 107 in the caps to reach into curved slots 109 formed in the exterior of the mounting half 20b. The prongs rotationally couple the dial 101 and the cap 102 (with the curved slots 109 guiding and limiting the rotation of the dial about the throw axis). A recess 113 with a hexagonal cross-section in the cap 102 receives a head of the tension screw 103 so as to rotationally couple the cap to the tension screw 103. An annular formation 110 in the cap seals the tension screw 103 in hole 106 that leads to the opening 105. Thus, by rotating the dial 101, the tension screw 103 can be advanced or withdrawn from the friction nut 80 to either tighten or loosen the contact between the pulley arm 31 and the interior of the housing half 20b at the washer 81.

In use, a user rotates the deflection sensitivity knob 24 to set the deflection sensitivity of the deflection arm 18 and correspondingly the maximum degree of deflection of the catheter tip section 14. With greater deflection sensitivity, the deflection arm 18 is more sensitive to rotation manipulations by the user, although the maximum degree of deflection in the tip section 14 is decreased. That is, with a greater pulley separation distance, the deflection assembly and thus tip deflection are more sensitive to deflection arm rotation. Thus, a tip deflection requires less deflection arm rotation.

In contrast, with lesser deflection sensitivity, a comparable tip deflection requires more deflection arm rotation because the deflection arm 18 is less sensitive to rotation manipulations by the user, although the maximum degree of deflection in the tip section 14 is increased. That is, with a lesser puller separation, the deflection assembly and thus tip deflection are less sensitive to deflection arm rotation.

The user can also rotate the dial 101 to set the tension of the deflection arm 18. With greater tension, more resistance to rotation is present and therefore more force is needed to rotate the deflection arm 18. With lesser tension, less resistance to rotation is present and therefore less force is needed to rotate the deflection arm. To deflect the tip section to one side of the catheter, the user rotates the deflection arm 18 to that side. To deflect the tip section to the other side, the user rotates the deflection 18 to that side. Any of the foregoing adjustments can be made in any order, and whether the catheter is inside or outside the patient's body, as needed or desired.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, features described or illustrated in one embodiment of the present invention may be incorporated in other embodiments of the present invention as needed or desired. Moreover, the cam device may have other embodiments that suitable interact with the pulleys to change their separation distance.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A bi-directional catheter comprising:
   a catheter body;
   a deflectable tip section distal the catheter body;
   tensile puller members; and
   a control handle proximal the catheter body, the control handle having:
      a deflection member adapted for user manipulation;
      a deflection assembly responsive to the deflection member to draw on one of the tensile puller members for deflecting the tip section, wherein the deflection assembly comprises two diametrically opposed pulleys separated from each other by a diametric separation distance which is adjustable between a maximum diametric separation for minimum deflection sensitivity in the deflection member and a minimum diametric separation for maximum deflection sensitivity in the deflection member; and
      a deflection sensitivity knob adapted to adjust sensitivity of the deflection member to manipulation of the deflection member by adjusting the diametric separation distance between the two pulleys.

2. A catheter of claim 1, wherein the deflection sensitivity knob correspondingly adjusts a maximum degree of deflection of the deflection tip section.

3. A catheter of claim 1, wherein the deflection assembly further includes a pulley arm adapted to rotate about a rotation axis wherein the two pulleys are located at opposite positions across the rotation axis.

4. A catheter of claim 3, wherein a respective one of the tensile puller members is actuated by action of the pulley arm on a respective one of the two pulleys to deflect the tip section.

5. A catheter of claim 3, wherein the deflection sensitivity knob includes a cam device adapted to change the separation distance.

6. A catheter of claim 1, wherein the deflection sensitivity knob includes a cam device adapted to act on the deflection assembly.

7. A catheter of claim 6, wherein the cam device is within a pulley arm of the deflection assembly.

8. A catheter of claim 1, wherein each of the tensile puller members includes a fiber portion that extends through the deflection assembly.

9. A catheter of claim 1, further comprising a deflection arm tension adjustment mechanism adapted for user adjustment of a tension of the deflection member, wherein greater tension results in greater resistance to rotation of the deflection member, and lesser tension results in lesser resistance to rotation of the deflection member.

10. A catheter adapted for bi-directional deflection, the catheter comprising:
a catheter body;
a tip section distal the catheter body;
a deflection member adapted for user manipulation;
a control handle proximal the catheter body; and
first and second tensile puller members extending between the tip section and the control handle, wherein the control handle includes: a deflection assembly responsive to the deflection member to draw on one of the first or second tensile puller members for deflecting the tip section, the deflection assembly having a pulley arm rotatable about an axis, the deflection assembly including two pulleys at diametrically opposed locations across the axis and separated from each other by a diametric separation distance which is adjustable between a maximum diametric separation for minimum deflection sensitivity in the deflection member and a minimum diametric separation for maximum sensitivity in the deflection member, each of the first and second tensile puller members extending through the deflection assembly and trained on a respective one of the two pulleys for deflecting the tip section; and
a deflection sensitivity knob including a cam device adapted to adjust the diametric separation distance between the pulleys.

11. A catheter of claim 10, wherein the control handle further comprises a deflection arm tension adjustment mechanism adapted to enable adjustment of resistance of the deflection member to rotation.

12. A catheter of claim 11, wherein the deflection assembly, the deflection sensitivity knob and the deflection arm tension adjustment mechanism share a common axis of rotation.

13. A catheter of claim 10, wherein each of the tensile puller members has a fiber portion that extends through the deflection assembly.

14. A catheter of claim 10, wherein the cam device is positioned between the pulleys and the cam device has extended portions in contact with the pulley that change the separation distance upon rotation of the cam device.

15. A catheter of claim 10, wherein the cam device is positioned between the pulleys and each of the pulleys has at least one linkage in contact with the cam device such that rotation of the cam device changes the separation distance.

16. A catheter of claim 10, wherein the pulleys are biased against separation from each other.

17. A catheter of claim 10, wherein the deflection assembly and the deflection sensitivity knob share a common axis of rotation.

18. A catheter of claim 10, wherein the cam device is positioned inside the deflection assembly.

* * * * *

UNITED STATES PATENT AND TRADEMARK OFFICE
CERTIFICATE OF CORRECTION

| | |
|---|---|
| PATENT NO. | : 8,137,308 B2 |
| APPLICATION NO. | : 12/211728 |
| DATED | : March 20, 2012 |
| INVENTOR(S) | : Jeffrey William Schultz |

It is certified that error appears in the above-identified patent and that said Letters Patent is hereby corrected as shown below:

In the Claims

Column 8, Claim 2, line 52.     Delete "deflection"
                                Insert -- deflectable --

Signed and Sealed this
Twenty-fourth Day of July, 2012

David J. Kappos
*Director of the United States Patent and Trademark Office*